(12) United States Patent
Kawamura et al.

(10) Patent No.: US 9,428,422 B2
(45) Date of Patent: Aug. 30, 2016

(54) COLORED TRANSLUCENT ZIRCONIA SINTERED BODY AND ITS USE

(71) Applicant: TOSOH CORPORATION, Yamaguchi (JP)

(72) Inventors: Kiyotaka Kawamura, Yamaguchi (JP); Hiroyuki Fujisaki, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 14/651,375

(22) PCT Filed: Dec. 26, 2013

(86) PCT No.: PCT/JP2013/084973
§ 371 (c)(1),
(2) Date: Jun. 11, 2015

(87) PCT Pub. No.: WO2014/104236
PCT Pub. Date: Jul. 3, 2014

(65) Prior Publication Data
US 2015/0315086 A1    Nov. 5, 2015

(30) Foreign Application Priority Data

Dec. 28, 2012 (JP) ................... 2012-286955
Dec. 28, 2012 (JP) ................... 2012-286957
Aug. 26, 2013 (JP) ................... 2013-174623

(51) Int. Cl.
| | |
|---|---|
| C04B 35/486 | (2006.01) |
| C04B 35/488 | (2006.01) |
| A61K 6/02 | (2006.01) |
| A61K 6/00 | (2006.01) |
| C04B 35/626 | (2006.01) |
| C04B 35/645 | (2006.01) |
| A61C 7/14 | (2006.01) |
| A61C 13/00 | (2006.01) |

(52) U.S. Cl.
CPC ......... *C04B 35/4885* (2013.01); *A61K 6/0005* (2013.01); *A61K 6/024* (2013.01); *C04B 35/486* (2013.01); *C04B 35/6262* (2013.01); *C04B 35/62655* (2013.01); *C04B 35/6455* (2013.01); *A61C 7/14* (2013.01); *A61C 13/0022* (2013.01); *C04B 2235/3217* (2013.01); *C04B 2235/3224* (2013.01); *C04B 2235/3225* (2013.01); *C04B 2235/3244* (2013.01); *C04B 2235/3272* (2013.01); *C04B 2235/3275* (2013.01); *C04B 2235/5409* (2013.01); *C04B 2235/5436* (2013.01); *C04B 2235/5445* (2013.01); *C04B 2235/6562* (2013.01); *C04B 2235/72* (2013.01); *C04B 2235/76* (2013.01); *C04B 2235/77* (2013.01); *C04B 2235/785* (2013.01); *C04B 2235/9653* (2013.01); *C04B 2235/9661* (2013.01)

(58) Field of Classification Search
CPC .. C04B 35/486; C04B 35/4885; A61K 6/024
See application file for complete search history.

(56) References Cited

U.S. PATENT DOCUMENTS

| | | | |
|---|---|---|---|
| 6,713,421 B1 | 3/2004 | Hauptmann et al. | |
| 7,538,055 B2 * | 5/2009 | Tsukuma | A61C 7/14 264/604 |
| 9,212,065 B2 * | 12/2015 | Yamada | C01G 25/02 |
| 2011/0027742 A1 | 2/2011 | Fujisaki et al. | |

FOREIGN PATENT DOCUMENTS

| | | |
|---|---|---|
| JP | 62-59571 | 3/1987 |
| JP | 4-2658 | 1/1992 |
| JP | 4-280864 | 10/1992 |
| JP | 9-188562 | 7/1997 |
| JP | 2005-289721 | 10/2005 |
| JP | 2006-298711 | 11/2006 |
| JP | 2008-50246 | 3/2008 |
| JP | 2008-50247 | 3/2008 |
| JP | 2011-20875 | 2/2011 |
| WO | 2009/125793 | 10/2009 |
| WO | 2012/125885 | 9/2012 |
| WO | 2013/018728 | 2/2013 |

OTHER PUBLICATIONS

International Search Report issued in PCT/JP2013/084973, dated Apr. 1, 2014.
International Preliminary Examination Report in PCT/JP2013/084973 issued Jun. 30, 2015.
Huang et. al.; "Effect of three kinds of rare earth oxides on chromaticity and mechanical properties of zirconia ceramic"; Chinese Journal of Stomatology; vol. 41, No. 6; Jun. 2006; pp. 327-330 with English translation herewith.

* cited by examiner

*Primary Examiner* — Karl Group
(74) *Attorney, Agent, or Firm* — Greenblum & Bernstein, P.L.C.

(57) ABSTRACT

A pink-colored zirconia sintered body has a high sintered body density and strength, and a colored translucency, which has a color tone similar to teeth and excellent translucency and has high aesthetic properties. A colored translucent zirconia sintered body includes from 2 to 4 mol % of yttria, from 0.02 to 0.8 mol % of $Er_2O_3$, at least 20 and less than 2,000 ppm, as calculated as $Fe_2O_3$, of an iron compound, at least 0.005 and less than 0.2 wt % of $Al_2O_3$ and the rest being zirconia, and having a lightness L* of from 55 to 75, a* of from 0 to 10 and b* of from 0 to 30 as chromatic parameters stipulated in JIS-Z8729, has a relative density of at least 99.80% and has a total light transmittance of at least 18% and at most 40% as measured at a sample thickness of 1 mm using a D65 light source.

18 Claims, No Drawings

COLORED TRANSLUCENT ZIRCONIA SINTERED BODY AND ITS USE

TECHNICAL FIELD

The present invention relates to a colored translucent zirconia sintered body and a pink-colored zirconia sintered body, which have a high sintered body density and strength, and a color tone quite similar to teeth and which are excellent in translucency. The colored translucent zirconia sintered body is useful particularly for dental applications and is further suitable for use as an orthodontic bracket or a mill blank for denture material. Whereas, the pink-colored zirconia sintered body is suitable for use as a decorative member or an exterior package for electronic material.

BACKGROUND ART

A zirconia sintered body having a small amount of $Y_2O_3$ (yttria) solid-solubilized as a stabilizer, has high strength and high toughness and thus is widely used as a material for a mechanical structure such as a cutoff tool, a die, a nozzle or a bearing, or as a biomaterial such as a dental material. In recent years, a zirconia sintered body having high strength has been used as a dental material, and in order to bring its color tone close to the color tone of natural teeth, it has been common to laminate another material on the surface of the zirconia sintered body and to adjust its aesthetic properties. However, along with the progress of utilization of the zirconia sintered body in the dental field, there has been an increasing demand for a zirconia sintered body which is useful as it is as a dental material without necessity to laminate another material.

In order to use a zirconia sintered body as it is as a dental material, both of translucency and coloration (color tone) are required. Heretofore, a zirconia sintered body having an ivory color close to natural teeth has been disclosed (e.g. Patent Document 1). In this Patent Document, addition of $Pr_6O_{11}$ and ZnO to a zirconia sintered body is essential, and there is no disclosure about translucency.

Further, a zirconia sintered body having a sintered body density of 99.8% and having translucency with a composition comprising 3 mol % of $Y_2O_3$ and 0.25 wt % of $Al_2O_3$ (alumina) has been disclosed (e.g. Patent Documents 2 and 3). However, the zirconia sintered body disclosed therein is one containing no colorant, and thus, heretofore, a zirconia sintered body which is colored and yet has high translucency, has not been in existence.

Patent Document 4 discloses a translucent zirconia sintered body colored to have a yellowish color tone by addition of Fe. By imparting a yellowish color tone, a color tone approximate to natural teeth was obtainable, but it was inadequate in a reddish or blackish tinge. By laminating another material on its surface to bring the color tone close to natural teeth, it was possible to use it, but it was not possible to use it as it is, since the difference in color tone from natural teeth was large.

By virtue of its high strength, a zirconia sintered body has been used mainly as a structural member or grinding media. However, from its beautiful surface gloss after mirror polishing, its application to a decorative member or an exterior package for electronic material is now expected. In order to meet with such broadened application, a colored zirconia sintered body which is excellent in aesthetic properties and has high strength, is desired.

Heretofore, as pink-colored zirconia sintered bodies, ones employing various additives have been proposed, but there has been none which has necessarily sufficient aesthetic properties. Particularly, zirconia has had such a problem that a colorant is hardly uniformly solid-solubilized therein, as compared with alumina, whereby a clear color tends to be hardly obtainable, or that the additive amount is relatively large so that it can hardly be sintered, whereby the properties of the sintered body, particularly the mechanical strength, tend to deteriorate.

Heretofore, the following ones have, for example, been proposed as pink-colored zirconia sintered bodies.

Patent Document 5 discloses a pink-colored zirconia sintered body having from 0.5 to 2 mol % of $Er_2O_3$ and from 0.1 to 0.6 mol % of ZnO incorporated to zirconia containing a stabilizer. Such a sintered body is one containing zinc oxide and further another coloring assistant, as essential components.

Further, Patent Document 6 discloses a pink-colored sintered body comprising from 2 to 5 mol % of $Y_2O_3$ as a stabilizer, and from 1 to 3 wt % (from about 0.3 to 0.9 mol %) of $Er_2O_3$.

Further, Patent Document 7 proposes a zirconia sintered body comprising from 0.6 to 1.2 mol % of $Y_2O_3$ as a stabilizer, and from 1.4 to 1.8 mol % of $Er_2O_3$.

PRIOR ART DOCUMENTS

Patent Documents

Patent Document 1: JP-A-4-280864
Patent Document 2: JP-A-2008-50247
Patent Document 3: WO2009/125793
Patent Document 4: WO2013/018728
Patent Document 5: JP-A-4-2658
Patent Document 6: JP-A-2011-20875
Patent Document 7: JP-A-09-188562

DISCLOSURE OF INVENTION

Technical Problems

The present invention is to solve the problems in the conventional methods as in Patent Documents 1 to 4 and to provide a colored zirconia sintered body which has a high sintered body density and strength and is excellent in translucency, particularly such a zirconia sintered body which can be produced by pressureless sintering. Further, with respect to zirconia sintered bodies as disclosed in Patent Documents 5 and 6, there have been demands from the market for further improvement of the sintered density, for improvement of the mechanical strength, for improvement of hydrothermal deterioration resistance and for providing a more brilliantly colored zirconia sintered body. Therefore, it is an object of the present invention to provide a pink-colored zirconia sintered body which has a high sintered body density and strength, and further has high aesthetic properties.

Solution to Problems

The present inventors have found that when the type and content of a colorant for a zirconia sintered body are adjusted, it is possible to obtain a zirconia sintered body which satisfies both translucency and coloration equal to a color tone sample of natural teeth, and thus have arrived at accomplishing the present invention. Here, a color tone sample of natural teeth may, for example, be a shade guide "VITAPAN (registered trademark) classical" by VITA, or "Vintage Halo NCC shade guide" by Shofu Inc.

Further, the present inventors have found that when the types and contents of a stabilizer and a colorant for a zirconia sintered body are adjusted, it is possible to obtain a zirconia sintered body which satisfies both the pink color and strength for the zirconia sintered body, by pressureless sintering, and thus have arrived at accomplishing the present invention.

That is, the present invention resides in a colored translucent zirconia sintered body which comprises from 2 to 4 mol % of yttria, from 0.02 to 0.8 mol % of $Er_2O_3$, at least 20 and less than 2,000 ppm, as calculated as $Fe_2O_3$, of an iron compound, at least 0.005 and less than 0.2 wt % of $Al_2O_3$ and the rest being zirconia, and which has a lightness L* of from 55 to 75, a* of from 0 to 10 and b* of from 0 to 30 as chromatic parameters stipulated in JIS-Z8729, has a relative density of at least 99.80% and has a total light transmittance of at least 18% and at most 40% as measured at a sample thickness of 1 mm using a D65 light source; a colored translucent zirconia sintered body which comprises from 2 to 4 mol % of yttria, less than 0.01 wt %, as calculated as CoO, of cobalt oxide, at least 20 and less than 2,000 ppm, as calculated as $Fe_2O_3$, of an iron oxide, at least 0.005 and less than 0.2 wt % of $Al_2O_3$ and the rest being zirconia, and which has a lightness L* of from 50 to 75, a* of from −1 to 10 and b* of from 0 to 30 as chromatic parameters stipulated in JIS-Z8729, has a relative density of at least 99.80% and has a total light transmittance of at least 18% and at most 40% as measured at a sample thickness of 1 mm using a D65 light source; and a pink-colored zirconia sintered body which is stabilized solely by erbia ($Er_2O_3$) or stabilized by yttria ($Y_2O_3$) and erbia ($Er_2O_3$), further contains at least 0.005 wt % and less than 0.2 wt % of alumina, and contains, when stabilized solely by erbia, at least 2 mol % and less than 4 mol % of erbia, or, when stabilized by erbia and yttria, at least 0.1 mol % and less than 2 mol % of erbia and at least 1 mol % and less than 4 mol % of yttria, and which has a lightness L* of from 58 to 75, a* of from 3 to 20 and b* of from −8 to −4 as chromatic parameters stipulated in JIS-Z8729.

Advantageous Effects of Invention

The colored translucent zirconia sintered body of the present invention exhibits a color tone close to teeth, has a high density and high strength and further is excellent in translucency, and thus, it is one excellent as a zirconia sintered body to be used in dental applications, specifically as a sintered body to be used as an orthodontic bracket or a mill blank for denture material. A powder for the colored translucent zirconia sintered body of the present invention is one capable of producing a colored translucent zirconia sintered body having the above characteristics even by pressureless sintering or by pressure sintering such as HIP.

The pink-colored zirconia sintered body of the present invention has a high sintered body density and high strength and exhibits a pink color with high aesthetic properties. A zirconia powder for the pink-colored zirconia sintered body of the present invention is one capable of producing a pink-colored zirconia sintered body having the above characteristics even by pressureless sintering or by pressure sintering such as HIP.

DESCRIPTION OF EMBODIMENTS

Now, the colored translucent zirconia sintered body of the present invention will be described in further detail.

The colored translucent zirconia sintered body of the present invention is a colored translucent zirconia sintered body (hereinafter referred to as the zirconia sintered body A) which comprises from 2 to 4 mol % of yttria, from 0.02 to 0.8 mol % of $Er_2O_3$, at least 20 and less than 2,000 ppm, as calculated as $Fe_2O_3$, of an iron compound, at least 0.005 and less than 0.2 wt % of $Al_2O_3$ and the rest being zirconia, and which has a lightness L* of from 55 to 75, a* of from 0 to 10 and b* of from 0 to 30 as chromatic parameters stipulated in JIS-Z8729, has a relative density of at least 99.80% and has a total light transmittance of at least 18% and at most 40% as measured at a sample thickness of 1 mm using a D65 light source.

The colored translucent zirconia sintered body A of the present invention contains from 2 to 4 mol %, preferably from 2.5 to 3.5 mol %, of yttria as a stabilizer. If the stabilizer is less than 2 mol %, the strength tends to be low, and the crystal phase tends to be unstable. On the other hand, if it exceeds 4 mol %, the sintered body strength tends to be low.

Yttria contained in the zirconia sintered body A may be one which becomes yttria after sintering, and a yttrium compound to be used before sintering is not particularly limited, and may, for example, be a soluble compound such as yttrium chloride or yttrium nitrate, or an insoluble compound such as yttrium oxide. It is preferred to add and dissolve the yttrium compound in a zirconia sol.

The colored translucent zirconia sintered body A of the present invention contains a colorant, and components constituting the colorant essentially include $Er_2O_3$ and an iron compound to color zirconia. The content of $Er_2O_3$ is from 0.02 to 0.8 mol %, preferably from 0.05 to 0.7 mol %. The content of the iron compound is at least 20 ppm and less than 2,000 ppm as calculated as $Fe_2O_3$, preferably at least 100 ppm and less than 1,500 ppm as calculated as $Fe_2O_3$.

$Er_2O_3$ contained in the zirconia sintered body A may be one which becomes $Er_2O_3$ after sintering, and an erbium compound to be used before sintering is not particularly limited, and may, for example, be a soluble compound such as erbium chloride or erbium nitrate, or an insoluble compound such as erbium oxide. It is preferred to add and dissolve the erbium compound in a zirconia sol. The reason is such that if an erbium compound is added during grinding of a zirconia powder, particles are likely to abnormally grow locally to form a zirconia sintered body having a low sintered body density or low strength.

When an erbium compound is uniformly dissolved, it may be contained together with a yttrium compound as a stabilizer. A zirconia powder stabilized solely by an erbium compound may be used as mixed with another zirconia powder stabilized with a yttrium compound. In the case of a zirconia powder stabilized solely by an erbium compound, preferred is a zirconia powder containing from 2 to 4 mol % of an erbium compound, so that by mixing with another zirconia powder stabilized with a yttrium compound, the content of the erbium compound may be adjusted to be less than 0.8 mol %.

The iron compound to be used before sintering for the zirconia sintered body A is not particularly limited, and may, for example, be a soluble compound such as iron chloride or iron nitride, or an insoluble compound such as iron oxide or iron oxide-hydroxide. In the case of using an insoluble compound, it is preferred that during grinding of a zirconia powder, an iron compound having an average particle size of at most 1 μm is added, dispersed and mixed. The reason is such that if at any other time, an insoluble iron compound is added and merely stirred and mixed, the sintered body will be speckled by the presence of aggregates, whereby the color tone tends to be non-uniform, or the zirconia sintered body tends to have low strength.

The colored translucent zirconia sintered body A of the present invention is one which further contains $Al_2O_3$ (alumina). As it contains alumina, the hydrothermal deterioration resistance of the zirconia sintered body will be improved. The content of alumina is at least 0.005 and less than 0.2 wt %, preferably at least 0.005 and at most 0.15 wt %.

If the alumina content in the colored translucent zirconia sintered body A of the present invention becomes 0.2 wt % or more, high densification tends to be difficult, and scattering of light is likely to occur due to the presence of alumina particles in the sintered body, whereby transmitted light tends to be hardly obtainable. If it is less than 0.005 wt %, deterioration in the hydrothermal deterioration resistance and decoloration of the color tone of the sintered body are likely to occur.

The colored translucent zirconia sintered body A of the present invention has a lightness $L^*$ of from 55 to 75, $a^*$ of from 0 to 10 and $b^*$ of from 0 to 30 as chromatic parameters stipulated in JIS-Z8729. If the lightness $L^*$, the value $a^*$ and the value $b^*$ are outside the above ranges, it tends to be difficult to obtain a color tone close to teeth. From the viewpoint of aesthetic properties, a preferred value $L^*$ is from 50 to 75, a preferred value $a^*$ is from 0 to 7, and a preferred value $b^*$ is from 10 to 27.

The relative density of the colored translucent zirconia sintered body A of the present invention is at least 99.80%, preferably at least 99.89%, further preferably at least 99.95%. If the relative density is less than 99.80%, the translucency tends to be low, and the zirconia sintered body tends to be poor in aesthetic properties as dental material. The upper limit value for the relative density is 100%.

The colored translucent zirconia sintered body A of the present invention is one which has a total light transmittance of at least 18% and at most 40% as measured at a sample thickness of 1 mm using a D65 light source. With a colored zirconia sintered body having a dark color tone and a low value of lightness $L^*$, the total light transmittance tends to be low. The translucency of the colored zirconia sintered body having a high sintered body density obtainable by the present invention, has high lightness $L^*$ and equal translucency as compared with a zirconia sintered body having a high sintered body density, and has aesthetic properties equal to natural teeth.

Further, the colored translucent zirconia sintered body A of the present invention preferably has a crystal grain size of from 0.35 to 0.50 μm. If the crystal grain size is less than 0.35 μm, many fine pores tend to be present among particles, whereby the relative density may not reach 99.8%. Further, it the crystal grain size exceeds 0.50 μm, there may be a case where the hydrothermal deterioration of the sintered body proceeds remarkably whereby the sintered body is likely to be ruptured, such being undesirable.

In the colored translucent zirconia sintered body A of the present invention, abnormally grown crystal grains (abnormally grown grains) are not present, and the sintered body is constituted by crystal grains having a uniform grain size. Here, the abnormally grown grains are meant for grains, of which sizes became at least 5 times the average grain size, and they are likely to be formed mainly by segregation of a stabilizer, whereby the crystal phase of grains tends to be cubic and thus tends to cause low strength.

The colored translucent zirconia sintered body A of the present invention preferably contains a tetragonal crystal phase and preferably consists of a single phase of tetragonal system, whereby the mechanical strength tends to be high. The colored translucent zirconia sintered body A of the present invention preferably has a three-point bending strength of at least 1,000 MPa. Further, the three-point bending strength is preferably at most 1,200 MPa. A more preferred strength is at least 1,100 MPa.

The colored translucent zirconia sintered body A of the present invention preferably has a monoclinic phase transformation depth of from 0 to 15 μm after immersion in hot water of 140° C. for 24 hours. If the monoclinic phase transformation depth exceeds 15 μm, hydrothermal deterioration of the sintered body tends to proceed to rupture the sintered body. A more preferred monoclinic phase transformation depth is at most 10 μm. Here, for the monoclinic phase transformation depth, a sintered body is cut, and its cross-section is observed by a scanning electron microscope (SEM), whereby the state of transformation of the crystal phase can be observed.

The colored translucent zirconia sintered body A of the present invention may contain a compound to be solid-solubilized in zirconia in order to finely adjust the color tone. The compound to be solid-solubilized in zirconia, may, for example, be an oxide of at least one member selected from Group 3a (Group 3), Group 5a (Group 5), Group 6a (Group 6), Group 7a (Group 6), Group 7a (Group 7), Group 8 (Groups 8 to 10) and Group 3b (Group 13) of the Periodic Table (inside of the brackets ( ) is the designation by IUPAC).

Further, the colored translucent zirconia sintered body of the present invention is a colored translucent zirconia sintered body (hereinafter referred to as the zirconia sintered body B) which comprises from 2 to 4 mol % of yttria, less than 0.01 wt %, as calculated as CoO, of cobalt oxide, at least 20 and less than 2,000 ppm, as calculated as $Fe_2O_3$, of an iron oxide, at least 0.005 and less than 0.2 wt % of $Al_2O_3$ and the rest being zirconia, and which has a lightness $L^*$ of from 50 to 75, $a^*$ of from −1 to 10 and $b^*$ of from 0 to 30 as chromatic parameters stipulated in JIS-Z8729, has a relative density of at least 99.80% and has a total light transmittance of at least 18% and at most 40% as measured at a sample thickness of 1 mm using a D65 light source.

Here, with respect to yttria, $Fe_2O_3$ and $Al_2O_3$, the same ones as used in the zirconia sintered body A may be used. In the zirconia sintered body B, the preferred contents as calculated as yttria, $Fe_2O_3$ and $Al_2O_3$, and the raw material compounds to be used before sintering, are the same as in the zirconia sintered body A.

The zirconia sintered body B contains less than 0.01 wt %, as calculated as CoO, of cobalt oxide, and the cobalt oxide content is preferably at most 0.075 wt % and preferably at least 0.005 wt %.

The cobalt oxide to be contained in the zirconia sintered body B may be one which becomes cobalt oxide after sintering, and a cobalt compound to be used before sintering is not particularly limited and may, for example, be a soluble compound such as cobalt chloride or cobalt nitride, or an insoluble compound such as cobalt oxide. In the case of using an insoluble compound, it is preferred that during grinding of a zirconia powder, a cobalt compound having an average particle size of at most 1 μm is added, dispersed and mixed. The reason is the same as in the case of the iron compound.

The colored translucent zirconia sintered body B of the present invention has a lightness $L^*$ of from 50 to 75, $a^*$ of from −1 to 10 and $b^*$ of from 0 to 30 as chromatic parameters stipulated in JIS-Z8729. If the lightness $L^*$, the value a* and the value b* are outside the above ranges, it tends to be difficult to obtain a color tone closer to teeth. From the viewpoint of aesthetic properties, a preferred value L* is from 50 to 75, a preferred value a* is from −1 to 7, and a preferred value b* is from 10 to 27.

Further, the relation between the value a* and the value b* is preferably the following relation.

$$a^* > 0.0123b^{*2} - 0.0598b^* - 2.9088$$

The relative density of the colored translucent zirconia sintered body B of the present invention is at least 99.80%, preferably at least 99.89%, further preferably at least 99.95%. If the relative density is less than 99.80%, the translucency tends to be low, and the zirconia sintered body tends to be poor in aesthetic properties as dental material.

The colored translucent zirconia sintered body B of the present invention is one which has a total light transmittance of at least 18% and at most 40% as measured at a sample thickness of 1 mm. With a colored zirconia sintered body having a dark color tone and a low value of lightness L*, the total light transmittance tends to be low. The translucency of the colored zirconia sintered body having a high sintered body density obtainable by the present invention, has high lightness L* and equal translucency as compared with a zirconia sintered body having a high sintered body density, and has aesthetic properties equal to natural teeth.

Further, the colored translucent zirconia sintered body B of the present invention preferably has a crystal grain size of from 0.35 to 0.50 μm. If the crystal grain size is less than 0.35 μm, many fine pores tend to be present among particles, whereby the relative density may not reach 99.8%. Further, it the crystal grain size exceeds 0.50 μm, there may be a case where the hydrothermal deterioration of the sintered body proceeds remarkably whereby the sintered body is likely to be ruptured, such being undesirable.

In the colored translucent zirconia sintered body B of the present invention, abnormally grown crystal grains (abnormally grown grains) are not present, and the sintered body is constituted by crystal grains having a uniform grain size. Here, the abnormally grown grains are meant for grains, of which sizes became at least 5 times the average grain size, and they are likely to be formed mainly by segregation of a stabilizer, whereby the crystal phase of grains tends to be cubic and thus tends to cause low strength.

The colored translucent zirconia sintered body B of the present invention preferably contains a tetragonal crystal phase and preferably consists of a single phase of tetragonal system, whereby the mechanical strength tends to be high. The colored translucent zirconia sintered body B of the present invention preferably has a three-point bending strength of at least 1,000 MPa. Further, the three-point bending strength is preferably at most 1,200 MPa. A more preferred strength is at least 1,100 MPa.

The colored translucent zirconia sintered body B of the present invention preferably has a monoclinic phase transformation depth of at most 15 μm after immersion in hot water of 140° C. for 24 hours. If the monoclinic phase transformation depth exceeds 15 μm, hydrothermal deterioration of the sintered body tends to proceed to rupture the sintered body. A more preferred monoclinic phase transformation depth is at most 10 μm. Here, for the monoclinic phase transformation, a sintered body is cut, and its cross-section is observed by a scanning electron microscope (SEM), whereby the state of transformation of the crystal phase can be observed.

The colored translucent zirconia sintered body B of the present invention may contain from 0.02 to 0.8 mol % of $Er_2O_3$ as a part of the rest being zirconia. As such $Er_2O_3$, the same one as used in the zirconia sintered body A may be used.

The colored translucent zirconia sintered body B of the present invention may contain a compound to be solid-solubilized in zirconia in order to finely adjust the color tone. The compound to be solid-solubilized in zirconia, may, for example, be an oxide of at least one member selected from Group 3a (Group 3), Group 5a (Group 5), Group 6a (Group 6), Group 7a (Group 6), Group 7a (Group 7), Group 8 (Groups 8 to 10) and Group 3b (Group 13) of the Periodic Table (inside of the brackets ( ) is the designation by IUPAC).

Now, a method for producing the colored translucent zirconia sintered body A or B of the present invention will be described.

The zirconia powder to be used for the production of the colored translucent zirconia sintered body A or B of the present invention preferably has a BET specific surface area within a range of from 10 to 15 m²/g. If the BET specific surface area of the zirconia powder becomes smaller than 10 m²/g, the powder sometimes tends to be one which can hardly be sintered at a low temperature, and if it becomes larger than 15 m²/g, the powder may sometimes be one having remarkable cohesion among particles. The BET specific surface area is particularly preferably within a range of from 11 to 14 m²/g.

The zirconia powder preferably has an average particle size within a range of from 0.4 to 0.7 μm. If the average particle size of the zirconia powder becomes smaller than 0.4 μm, fine particles to increase the aggregation property of the powder tend to increase, whereby molding tends to be difficult. On the other hand, if it is larger than 0.7 μm, coarse particles containing hard aggregated particles tend to increase, whereby molding tends to be difficult, and the coarse particles hinder sintering densification, whereby the sintering property tends to be poor. A preferred average particle size is from 0.4 to 0.6 μm. Further, the maximum particle size of the zirconia powder is preferably at most 2.0 μm, more preferably at most 1.5 μm.

The zirconia powder has a sintering shrinkage rate ($\Delta\rho/\Delta T$:g/cm³·° C.) in a relative density range of from 70% to 90% (hereinafter referred to simply as "sintering shrinkage rate") of preferably from 0.012 to 0.016 in pressureless sintering at a temperature raising rate of 300° C./hr in the air. The sintering shrinkage rate is an index for the sintering property of the zirconia powder. When the sintering shrinkage rate is within this range, a zirconia powder excellent in the sintering property will be obtained. Here, the sintering shrinkage rate is a value measured at a relative density of at least 70%. Therefore, the sintering shrinkage rate is not affected by fluctuations in the density of the green body. Further, the sintering shrinkage rate in a relative density range of from 70% to 90% is constant in its speed. Accordingly, the sintering shrinkage rate has a linear function of the temperature and the relative density, and therefore, it is possible to obtain an accurate sintering shrinkage rate without using a special approximation process.

The zirconia powder may be obtained, for example, by drying, calcining and grinding a hydrated zirconia sol obtainable by hydrolysis of an aqueous zirconium salt solution. Specifically, after adding an alkali metal hydroxide and/or an alkaline earth metal hydroxide to such an aqueous zirconium salt solution, hydrolysis may be carried out until the conversion becomes at least 98%, and to a hydrated zirconia sol thereby obtainable, yttrium and, if required erbium, may be added as a raw material for a stabilizer, followed by drying.

The zirconium salt to be used for the production of the hydrated zirconia sol, may, for example, be zirconium oxychloride, zirconium nitrate, zirconium chloride or zirconium sulfate, or a mixture of zirconium hydroxide and an acid may be used. The alkali metal hydroxide and/or the alkaline earth metal hydroxide may, for example, be a hydroxide of e.g. lithium, sodium, potassium, magnesium or calcium. Such a hydroxide is preferably added in the form of an aqueous solution.

The dried powder of the hydrated zirconia sol obtained as described above, may then be calcined at a temperature of from 1,000 to 1,200° C. to obtain a zirconia powder. If the calcination temperature is outside this range, the aggregation property of a powder obtainable under the following conditions of the present invention tends to be remarkably strong, or coarse particles containing hard aggregated particles tend to increase, whereby the average particle size of a slurry tends to be outside the range of from 0.4 to 0.7 μm, and there may be a case where it is difficult to obtain a zirconia powder. The calcination temperature is particularly preferably from 1,050 to 1,150° C.

Then, the calcined powder obtained as described above, is preferably subjected to wet grinding using zirconia balls so that the average particle size will be within a range of from 0.4 to 0.7 μm. By grinding the calcined powder obtained by calcination at the above calcination temperature so that the average particle size becomes from 0.4 to 0.7 μm, a zirconia powder having a BET specific surface area within a range of from 10 to 15 $m^2/g$ is obtainable. Further, the crystallite diameter at that time becomes from 25 to 40 nm, and a zirconia powder of which almost 100% is tetragonal phase after calcination becomes a zirconia powder of which from 30 to 50% is monoclinic phase.

In a case where aluminum is used in the production of the colored translucent zirconia sintered body of the present invention, the raw material compound may, for example, be alumina, hydrated alumina, alumina sol, aluminum hydroxide, aluminum chloride, aluminum nitrate or aluminum sulfate. Like a coloring element compound, it is preferred to use an insoluble compound.

In order to obtain a desired color tone zirconia sintered body, an iron compound and a cobalt compound as colorants may be added in necessary amounts to a zirconia powder stabilized with yttria and erbia, to prepare a colored zirconia powder, but it is also possible that a plurality of zirconia powders containing the respective colorants are preliminarily prepared, and in order to obtain a desired blend, the plurality of colored zirconia powders are mixed to change the colorant composition.

For example, a zirconia powder stabilized by 3 mol % of yttria is produced (powder 1). Separately, a zirconia powder stabilized by 3.2 mol % of erbia is produced (powder 2). Further, a powder having 1,500 ppm as calculated as $Fe_2O_3$ of an iron compound added to a zirconia powder stabilized by 3 mol % of yttria, and a powder having 0.05 wt % as calculated as CoO of a cobalt compound added to such a zirconia powder, are respectively produced (powders 3 and 4). Powders 1 to 4 contain at least 0.005 and less than 0.2 wt % of alumina. These four types of powders are mixed to be uniform and blended so that the contents of $Er_2O_3$, $Fe_2O_3$ and CoO as colorants become the desired concentrations, to obtain a zirconia sintered body, whereby it is possible to obtain a colored zirconia sintered body having the same color tone as in the case of sintering a colored zirconia powder wherein as colorants, an iron compound and a cobalt compound are added in necessary amounts to a zirconia powder stabilized by yttria and erbia.

As color tone samples of natural teeth, the shade guide "VITAPAN (registered trademark) classical" by VITA includes color tone samples of 16 colors, and by adjusting the blend proportions of the above four types of powders, all of the color tones can be reproduced.

At that time, by finely adjusting the physical properties (e.g. the BET specific surface areas) of the four types of powders to let the sintering shrinkage rate as an index for the sintering property be consistent as far as possible, it is possible to obtain a high density zirconia sintered body without lowering the density of the obtainable sintered body and also without impairing the translucency.

As the zirconia powder granules, it is preferred to use spray-granulated powder granules, or a spray-granulated powder containing an organic binder may be used.

By spray-drying a slurry of the zirconia powder, the fluidity at the time of forming a green body will be high, and air bubbles will be less likely to be formed in a sintered body. The granules preferably have a particle size of from 30 to 80 μm and an untamped density of from 1.10 to 1.40 $g/cm^3$.

In the case of using a binder for granulation, such a binder may, for example, be a common binder such as polyvinyl alcohol, polyvinyl butyrate, wax or an acrylic binder. Among them, an acrylic binder having a carboxy group or its derivative (e.g. a salt, particularly an ammonium salt) in its molecule is preferred. Such an acrylic binder may, for example, be polyacrylic acid, polymethacrylic acid, an acrylic acid copolymer, a methacrylic acid copolymer or a derivative thereof. The content of the binder is preferably from 0.5 to 10 wt %, more preferably from 1 to 5 wt %, to the zirconia powder in the zirconia powder slurry.

In order to obtain the colored translucent zirconia sintered body A or B of the present invention, it is preferred to form the zirconia powder into a green body having a relative density of about 50±5% by usual press-molding (as the case requires, by cold isostatic pressing (CIP treatment)), followed by sintering.

The production of the colored translucent zirconia sintered body A or B of the present invention is preferably carried out by sintering under pressureless at from 1,350 to 1,450° C., particularly at 1,400° C.

If the sintering temperature is less than 1,350° C., there may be a case where the relative density will not reach 99.80%, and if it exceeds 1,450° C., there may be a case where hydrothermal deterioration of the sintered body tends to remarkably proceed to cause a problem that the sintered body is susceptible to breakage.

The colored translucent zirconia sintered body A or B of the present invention is obtained by pressureless sintering, but the sintering atmosphere is not particularly limited unless it is a reducing atmosphere, and it may be an oxygen atmosphere or the atmospheric air. It is particularly preferred to carry out sintering in the atmospheric air.

Now, the pink-colored zirconia sintered body of the present invention will be described in further detail.

The pink-colored zirconia sintered body of the present invention is a zirconia sintered body which is stabilized solely by erbia ($Er_2O_3$) or stabilized by yttria ($Y_2O_3$) and erbia ($Er_2O_3$). The zirconia sintered body stabilized solely by erbia is one which contains at least 2 mol % and less than 4 mol % of erbia in the sintered body. If the content of erbia is less than 2 mol %, the strength tends to be low, and the crystal phase tends to be unstable. If the content is 4 mol % or more, the strength tends to be low. The content of erbia is preferably at least 2 mol % and less than 3.5 mol %.

On the other hand, the zirconia sintered body stabilized by yttria ($Y_2O_3$) and erbia ($Er_2O_3$) is one which contains at least 0.1 mol % and less than 2 mol % of erbia and at least 1 mol % and less than 4 mol % of yttria, in the sintered body.

If the content of erbia is less than 0.1 mol %, it tends to be difficult to obtain a zirconia sintered body having a pink color tone, and if the content is 2 mol % or more, the strength tends to be low. The content of erbia is preferably at least 0.2 mol % and less than 2.0 mol %. Further, if the content of yttria is less than 1 mol %, the strength tends to be low, and the crystal phase tends to be unstable, and if the content is 4 mol % or more, the strength tends to be low. The content of yttria is preferably at least 1.0 mol % and less than 3.5 mol %. Here, erbia functions not only as a stabilizer but also as a colorant, and yttria functions only as a stabilizer.

The erbium compound to be used for forming erbia in a zirconia sintered body is not particularly limited and may, for example, be a soluble compound such as erbium chloride or erbium nitrate, or an insoluble compound such as erbium oxide. The erbium compound is preferably added to and dissolved in a zirconia sol. The reason is such that if an erbium compound is added during grinding of a zirconia powder, aggregates will remain and particles are likely to abnormally grow locally to form a zirconia sintered body having a low sintered body density or low strength.

The yttrium compound to be used for forming yttria in a zirconia sintered body is not particularly limited and may, for example, be a soluble compound such as yttrium chloride or yttrium nitrate, or an insoluble compound such as yttrium oxide. The yttrium compound is preferably added to and dissolved in a zirconia sol. The reason is such that if a yttrium compound is added during grinding of a zirconia powder, aggregates will remain and particles are likely to abnormally grow locally to form a zirconia sintered body having a low sintered body density or low strength.

When an erbium compound is uniformly dissolved, it may be contained together with a yttrium compound as a stabilizer. A zirconia powder stabilized solely by an erbium compound may be used as mixed with another zirconia powder stabilized with a yttrium compound.

The pink-colored zirconia sintered body of the present invention has a lightness L* of from 58 to 75, a* of from 3 to 20 and b* of from −8 to −4 as chromatic parameters stipulated in JIS-Z8729. If the value a* is less than 3, it tends to be difficult to obtain a bright pink color tone. From the viewpoint of aesthetic properties, a preferred value b* is from −7 to −4.

In the pink-colored zirconia sintered body of the present invention, crystal grains which are abnormally grown (abnormally grown grains) are not present, and the zirconia sintered body is constituted by crystal grains having a uniform grain size. Here, the abnormally grown grains are meant for grains, of which sizes became at least 5 times the average grain size, and they are likely to be formed mainly by segregation of a stabilizer, whereby the crystal phase of grains tends to be cubic and thus tends to cause low strength.

The pink-colored zirconia sintered body of the present invention preferably contains a tetragonal crystal phase and particularly preferably consists of a single phase of tetragonal system, whereby the mechanical strength tends to be high. The pink-colored zirconia sintered body of the present invention preferably has a three-point bending strength of at least 1,000 MPa, more preferably at least 1,000 MPa and at most 1,300 MPa.

The pink-colored zirconia sintered body of the present invention preferably has a crystal grain size of from 0.35 to 0.50 μm in order to avoid hydrothermal deterioration and lowering of the relative density due to presence of fine pores among grains.

The pink-colored zirconia sintered body of the present invention preferably has a total light transmittance of at least 25%, more preferably from 26 to 40%, as measured at a sample thickness of 1 mm using a D65 light source.

Further, the relative density of the pink-colored zirconia sintered body of the present invention is preferably at least 99.80%, particularly preferably at least 99.90%.

The pink-colored zirconia sintered body of the present invention is one which further contains alumina. The content of alumina is at least 0.005 wt % and less than 0.2 wt %, preferably at least 0.005 wt % and at most 0.15 wt %.

If the alumina content in the pink-colored zirconia sintered body of the present invention is 0.2 wt % or more, high densification tends to be difficult, and it tends to be difficult to obtain translucency. On the other hand, if the alumina content is less than 0.005 wt %, hydrothermal deterioration resistance is likely to be deteriorated.

With a view to avoiding hydrothermal deterioration of the sintered body, the pink-colored zirconia sintered body of the present invention preferably has a monoclinic phase transformation depth of from 0 to 15 μm, more preferably from 0 to 10 μm, after immersion in hot water of 140° C. for 24 hours. Here, for the monoclinic phase transformation depth, a zirconia sintered body is cut, and its cross-section is observed by a scanning electron microscope (SEM), whereby the state of transformation of the crystal phase can be observed.

Now, a method for producing the pink-colored zirconia sintered body of the present invention will be described.

The zirconia powder to be used for the production of the pink-colored zirconia sintered body of the present invention preferably has a BET specific surface area within a range of from 10 to 15 $m^2/g$, particularly preferably within a range of from 11 to 14 $m^2/g$, from the viewpoint of low temperature sintering and cohesion among particles.

The zirconia powder to be used for the production of the pink-colored zirconia sintered body of the present invention preferably has an average particle size of the slurry within a range of from 0.4 to 0.7 μm, particularly preferably from 0.4 to 0.6 μm, with a view to reducing fine particles which increase the aggregation property of the powder and reducing coarse particles containing hard aggregated particles. Further, the maximum particle size of the zirconia slurry is preferably at most 2.0 μm, more preferably at most 1.5 μm.

The zirconia powder to be used for the production of the pink-colored zirconia sintered body of the present invention may be obtained, for example, by drying, calcining and grinding a hydrated zirconia sol obtainable by hydrolysis of an aqueous zirconium salt solution. Specifically, after adding an alkali metal hydroxide and/or an alkaline earth metal hydroxide to such an aqueous zirconium salt solution, hydrolysis may be carried out until the conversion becomes at least 98%, and to a hydrated zirconia sol thereby obtainable, it is preferred to add only an erbium compound, or a yttrium compound and an erbium compound, as raw material for a stabilizer and a colorant.

The zirconium salt to be used for the production of the hydrated zirconia sol, may, for example, be zirconium oxychloride, zirconium nitrate, zirconium chloride or zirconium sulfate, or a mixture of zirconium hydroxide and an acid may be used. The alkali metal hydroxide and/or the alkaline earth metal hydroxide to be added to the aqueous zirconium salt solution, may, for example, be a hydroxide of e.g. lithium, sodium, potassium, magnesium or calcium. Such a hydroxide is preferably added in the form of an aqueous solution.

The dried powder of the hydrated zirconia sol obtained as described above, may then be calcined at a temperature of preferably from 1,000 to 1,200° C., particularly preferably from 1,050 to 1,150° C., to obtain a zirconia powder, with a view to reducing fine particles which increase the aggregation property of a powder and reducing coarse particles containing hard aggregated particles.

Then, the calcined powder obtained as described above, is preferably subjected to wet grinding using zirconia balls so that the average particle size of the slurry will be within a range of from 0.4 to 0.7 µm.

The raw material compound for alumina to be incorporated to the pink-colored zirconia sintered body of the present invention, may, for example, be alumina, hydrated alumina, alumina sol, aluminum hydroxide, aluminum chloride, aluminum nitrate or aluminum sulfate. Like a coloring element compound, it is preferred to use an insoluble compound.

As the zirconia powder to be used for the production of the pink-colored zirconia sintered body of the present invention, it is preferred to use spray-granulated powder granules, or spray-granulated powder granules containing an organic binder in addition to yttria and erbia as a stabilizer and a colorant, and alumina as an additive, may be used.

By spray-drying a slurry of the zirconia powder, the fluidity at the time of forming a green body will be high, and air bubbles will be less likely to be formed in a zirconia sintered body. The zirconia granulated powder preferably has a particle size of from 30 to 80 µm and an untamped density of from 1.10 to 1.40 g/cm$^3$.

In the case of using a binder for granulation, such a binder may, for example, be a common binder such as polyvinyl alcohol, polyvinyl butyrate, wax or an acrylic binder. Among them, an acrylic binder having a carboxy group or its derivative (e.g. a salt, particularly an ammonium salt) in its molecule is preferred. Such an acrylic binder may, for example, be polyacrylic acid, polymethacrylic acid, an acrylic acid copolymer, a methacrylic acid copolymer or a derivative thereof. The content of the binder is preferably from 0.5 to 10 wt %, particularly preferably from 1 to 5 wt %, to the zirconia powder in the zirconia powder slurry.

In order to obtain the pink-colored zirconia sintered body of the present invention, it is preferred to form the zirconia powder into a green body having a relative density of about 50±5% by usual press-molding (as the case requires, by cold isostatic pressing (CIP treatment)), followed by sintering.

The production of the pink-colored zirconia sintered body of the present invention is preferably carried out by sintering under pressureless at from 1,350 to 1,450° C., particularly at 1,400° C., from the viewpoint of the relative density and hydrothermal deterioration resistance of the zirconia sintered body.

The pink-colored zirconia sintered body of the present invention is obtained by pressureless sintering, but the sintering atmosphere is not particularly limited unless it is a reducing atmosphere, and it may be an oxygen atmosphere or the atmospheric air. It is particularly preferred to carry out sintering in the atmospheric air.

Examples

Now, the present invention will be described specifically with reference to Examples, but it should be understood that the present invention is by no means restricted by these Examples.

In Examples, the average particle size of a zirconia slurry was measured by means of a MICROTRAC particle size distribution analyzer (Model: 9320-HRA, manufactured by Honeywell). As a pretreatment condition for a sample, a powder was suspended in distilled water and dispersed for 3 minutes by means of a ultrasonic homogenizer (model: US-150T, manufactured by Nippon Seiki Seisakusho).

Molding of a raw material powder was conducted by die pressing under a pressure of 19.6 MPa, and such a preliminary green body was put in a rubber mold and subjected to cold isostatic pressing (CIP) treatment under a pressure of 196 MPa to form a green body. The obtained green body was sintered at a predetermined temperature (retention time: two hours).

For the color tone of a zirconia sintered body, chromatic parameters L*, a* and b* as stipulated in JIS-Z8729 were measured. As the zirconia sintered body has translucency, for the measurement of the color tone, the thickness of the sintered body was unified to be 2.8 mm, and a mirror-polished surface was measured.

The density of a zirconia sintered body was measured by Archimedes' method.

The total light transmittance of a zirconia sintered body was measured in accordance with JIS K7361 by means of a turbidity meter (model: NDH2000, manufactured by Nippon Denshoku Industries Co., Ltd.) using light source D65. As a sample, one having a disk shape and a thickness of 1 mm obtained by polishing both surfaces of a zirconia sintered body was used.

The crystal grain size of a zirconia sintered body was calculated by the planimetric method by using a scanning electron microscope (SEM) (model: JSM-6390LV, manufactured by JEOL Ltd.), after subjecting the mirror-polished zirconia sintered body to a heat etching treatment. Specifically, a circle was drawn on the microscopic image so that the total of the number of particles inside circle $n_c$ and the number of particles on the circle $N_i$ becomes from 100 to 150, or when the number of particles on a single image was less than 100, a plurality of circles were drawn on a plurality of microscopic images so that the total of the number of particles ($n_c+N_i$) becomes from 100 to 150, thereby to obtain the crystal grain size by the planimetric method.

The three-point bending strength of a zirconia sintered body was evaluated by a three-point bending measuring method in accordance with JIS R1601.

The hydrothermal deterioration properties were evaluated by polishing the obtained sintered body until its one surface became a mirror surface, and then immersing it in a hot water of 140° C. for 24 hours, whereupon the transformation depth of the monoclinic phase formed, was obtained.

The transformation depth was obtained by cutting the immersion-treated sintered body, observing the cross section with a scanning electron microscope (SEM) (model: JSM-6390LV, manufactured by JEOL Ltd.), and measuring the depth at which the crystal organization became rough, from the mirror-polished surface.

Further, the "average particle size of a slurry" relating to the zirconia powder of the present invention is meant for a diameter of a sphere having the same volume as a particle with the median of the cumulative curve of the particle size distribution represented by a volume basis (median size; particle size corresponds to 50% of the cumulative curve) and is one measured by a particle size distribution measuring apparatus by a laser diffraction method.

The "stabilizer concentration" is a value of the ratio of stabilizer/($ZrO_2$+stabilizer), as represented by mol %.

The "additive content" is a value of the ratio of additive/($ZrO_2$+stabilizer+additive) as represented by wt %. Here, the additive is a value as calculated as an oxide.

The "relative density" is a value represented by the ratio (%) of ($\rho/\rho_0)\times100$) calculated by using the density $\rho$ measured by Archimedes' method and the density $\rho_0$ of HIP sintered body.

The "M phase ratio (fm)" is a value calculated by the following expression 1 after obtaining the diffraction intensities of the (111) and (11-1) faces of a monoclinic phase, the (111) face of a tetragonal phase, and the (111) face of a cubic phase, respectively, by a powder X-ray diffraction (XRD) measurement.

$$f_m(\%) = \frac{I_m(111) + I_m(11\text{-}1)}{I_m(111) + I_m(11\text{-}1) + I_t(111) + I_c(111)} \times 100$$

(wherein I represents the peak intensity of each diffraction peak, and the suffixes m, t and c represent a monoclinic phase, a tetragonal phase, and a cubic phase, respectively.)

Examples 1 to 8

Synthesis of Zirconia Granulated Powder Containing 0.05 wt % of Alumina and 3.0 Mol % of Yttria To a zirconium oxychloride aqueous solution, yttria was added to a $Y_2O_3$ concentration of 3 mol %, followed by hydrolysis to obtain a hydrated zirconia sol, which was then dried and calcined at a calcination temperature of 1,100° C. for 2 hours.

After washing the obtained calcined powder with water, α-alumina was mixed therewith to an alumina content of 0.05 wt %, and distilled water was added to obtain a slurry having a zirconia concentration of 45 wt %. This slurry was milled for 24 hours with a vibration mill using zirconia balls having a diameter of 3 mm.

The average particle size of the obtained slurry was 0.41 μm and the maximum particle size was ≤1.5 μm. The BET specific surface area of the dried zirconia powder was 13 m²/g, the crystallite diameter was 33 nm, and the M phase ratio of the dried powder was 40%. To the obtained slurry, an organic binder was added in an amount of 3 wt %, and then a spray-drying was carried out to obtain a zirconia granulated powder having an average particle size of 50 μm.
(Synthesis of Zirconia Granulated Powder Containing 0.05 wt % of Alumina, 3.0 Mol % of Yttria and 1,500 Ppm of Iron Oxide)

To a zirconium oxychloride aqueous solution, yttria was added to a $Y_2O_3$ concentration of 3 mol %, followed by hydrolysis to obtain a hydrated zirconia sol, which was then dried and calcined at a calcination temperature of 1,100° C. for 2 hours.

After washing the obtained calcined powder with water, α-alumina was added to an alumina content of 0.05 wt %, iron oxide-hydroxide was added to 1,500 ppm as calculated as $Fe_2O_3$, and distilled water was added to obtain a slurry having a zirconia concentration of 45 wt %. This slurry was milled for 24 hours with a vibration mill using zirconia balls having a diameter of 3 mm.

The average particle size of the obtained slurry was 0.42 μm and the maximum particle size was ≤1.5 μm. The BET specific surface area of the dried zirconia powder was 13 m²/g, the crystallite diameter was 33 nm, and the M phase ratio of the dried powder was 42%. To the obtained slurry, an organic binder was added in an amount of 3 wt %, and then a spray-drying was carried out to obtain a zirconia granulated powder having an average particle size of 48 μm.
(Synthesis of Zirconia Granulated Powder Containing 0.05 wt % of Alumina and 3.2 Mol % of Erbia)

To a zirconium oxychloride aqueous solution, erbia was added to an $Er_2O_3$ concentration of 3.2 mol %, followed by hydrolysis to obtain a hydrated zirconia sol, which was then dried and calcined at a calcination temperature of 1,100° C. for 2 hours.

After washing the obtained calcined powder with water, α-alumina was mixed therewith to an alumina content of 0.05 wt %, and distilled water was added to obtain a slurry having a zirconia concentration of 45 wt %. This slurry was milled for 24 hours with a vibration mill using zirconia balls having a diameter of 3 mm.

The average particle size of the obtained slurry was 0.42 μm and the maximum particle size was ≤1.5 μm. The BET specific surface area of the dried zirconia powder was 12 m²/g, the crystallite diameter was 34 nm, and the M phase ratio of the dried powder was 39%. To the obtained slurry, an organic binder was added in an amount of 3 wt %, and then a spray-drying was carried out to obtain a zirconia granulated powder having an average particle size of 45 μm.

The above three types of powders were mixed in an optional ratio in a plastic bottle to obtain a mixed powder having a $Y_2O_3$ concentration of from 2.85 to 2.92 mol %, an $Er_2O_3$ concentration of from 0.08 to 0.17 mol % and from 200 to 1,430 ppm as calculated as $Fe_2O_3$, of iron oxide-hydroxide.

The obtained mixed powder was molded by uniaxial pressing (19.6 MPa), then molded by CIP (196 MPa) and sintered (pressureless sintering) under conditions of a sintering temperature of 1,400° C. or 1,450° C., a temperature-rising rate of 600° C./hr, and a retention time of 2 hours, to obtain a colored translucent zirconia sintered body.

Examples 9 to 12

In Examples 9 to 12, the zirconia sintered body obtained by the pressureless sintering at 1,450° C., was further subjected to HIP treatment at a treating temperature of 1,400° C. under a pressure of 150 MPa, to obtain a colored translucent zirconia sintered body.

Between before and after the HIP treatment, there was no substantial change in the relative density and the total light transmittance of the colored translucent zirconia sintered body. It was thereby found that the colored translucent zirconia sintered body of the present invention is a sintered body having properties equal to one treated by HIP, without being subjected to HIP treatment.

COMPARATIVE EXAMPLES 1 to 3

The above two types of powders containing no $Er_2O_3$ were mixed in an optional ratio in a plastic bottle to obtain a mixed powder having a $Y_2O_3$ concentration of 3 mol % and from 200 or 450 ppm as calculated as $Fe_2O_3$, of iron oxide-hydroxide.

The obtained mixed powder was molded by uniaxial pressing (19.6 MPa), then molded by CIP (196 MPa) and sintered (pressureless sintering) under conditions of a sintering temperature of 1,400° C. or 1,450° C., a temperature-rising rate of 600° C./hr, and a retention time of 2 hours, to obtain a colored translucent zirconia sintered body.

It was found that with the colored translucent zirconia sintered body containing no $Er_2O_3$, the value a* decreased, and the reddish tone faded, whereby it was not possible to obtain a color tone of natural teeth.

Examples 13 to 16

A colored translucent zirconia sintered body was produced in the same manner as in Examples 1 to 8 except that the above three types of powders were mixed in an optional ratio in a plastic bottle to obtain a mixed powder having a $Y_2O_3$ concentration of from 2.40 to 2.70 mol % and an $Er_2O_3$ concentration of from 0.33 to 0.66 mol %.

Examples 17 to 20

In Examples 17 to 20, the zirconia sintered body obtained by the pressureless sintering at 1,450° C., was further subjected to HIP treatment at a treating temperature of 1,400° C. under a pressure of 150 MPa, to obtain a colored translucent zirconia sintered body.

The yttria amount, the $Er_2O_3$ amount, the Fe additive amount as $Fe_2O_3$, the alumina additive amount, the sintering temperature, and the measured density, relative density, total light transmittance by D65 light source, lightness value L*, value a* and value b* as chromatic parameters stipulated in JIS-Z8729, strength, crystal grain size and monoclinic phase transformation depth after immersion in hot water of 140° C. for 24 hours, of the colored translucent zirconia sintered body, in Examples 1 to 12 and Comparative Examples 1 to 3, are shown in the following Table 1, and the same numerical values in Examples 13 to 20 are shown in the following Table 2.

Examples 21 to 41

Synthesis of Zirconia Granulated Powder Containing 0.05 wt % of Alumina, 360 Ppm of Cobalt Oxide and 3.0 Mol % of Yttria To a zirconium oxychloride aqueous solution, yttria was added to a $Y_2O_3$ concentration of 3 mol %, followed by hydrolysis to obtain a hydrated zirconia sol, which was then dried and calcined at a calcination temperature of 1,100° C. for 2 hours.

After washing the obtained calcined powder with water, α-alumina was added to an alumina content of 0.05 wt %, cobalt oxide was added to 360 ppm as calculated as CoO, and distilled water was added to obtain a slurry having a zirconia concentration of 45 wt %. This slurry was milled for 24 hours with a vibration mill using zirconia balls having a diameter of 3 mm.

The average particle size of the obtained slurry was 0.41 μm and the maximum particle size was ≤1.5 μm. The BET specific surface area of the dried zirconia powder was 13 m²/g, the crystallite diameter was 32 nm, and the M phase ratio of the dried powder was 43%. To the obtained slurry, an organic binder was added in an amount of 3 wt %, and then a spray-drying was carried out to obtain a zirconia granulated powder having an average particle size of 47 μm.

The above powder and the three types of powders prepared in Examples 1 to 8 were mixed in a plastic bottle so that the composition would be as shown in Table 3, to obtain a mixed powder.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to obtain a colored translucent zirconia sintered body.

The "relative density" in Example 21 and subsequent Examples was calculated from theoretical density $\rho_0$ and measured density ρ by using the following formula (1). The measured density was obtained by Archimedes' method.

Relative density(%)=(ρ/ρ₀)×100    (1)

Further, the theoretical densities ρx, ρy and ρz of the sintered bodies in the respective compositions used for mixing, were calculated from the densities and concentrations of the added oxides by using the following formulae.

Theoretical density ρx of zirconia sintered body containing 0.05 wt % of alumina and 3.0 mol % of yttria =

$$100/[(0.05/\rho Al) + (99.95/\rho Zr)] = 6.0940 \text{ g/cm}^3$$

Theoretical density ρy of zirconia sintered body containing 0.05 wt % of alumina, 3.0 mol % of yttria and 1,500 ppm of iron oxide =

$$100/[(0.05/\rho Al) + (0.15/\rho Fe) + (99.80/\rho Zr)] = 6.0925 \text{ g/cm}^3$$

Theoretical density ρz of zirconia sintered body containing 0.05 wt % of alumina, 360 ppm of cobalt oxide and 3.0 mol % of yttria =

$$100/[(0.05/\rho Al) + (0.036/\rho Co) + (99.914/\rho Zr)] = 6.0941 \text{ g/cm}^3$$

where

ρAl: theoretical density of alumina; 3.99 g/cm³

ρFe: theoretical density of $Fe_2O_3$; 5.24 g/cm³

ρCo: theoretical density of CoO; 6.40 g/cm³

ρZr: theoretical density of zirconia containing 3.0 mol % of yttria; 6.0956 g/cm³

As the theoretical density of the zirconia sintered body containing 0.05 wt % of alumina and 3.2 mol % of erbia, HIP sintered body density of 6.336 g/cm³ was used.

From such theoretical densities and blend ratios of the sintered bodies in the respective compositions, theoretical density $\rho_0$ was calculated by using the following formula (2).

$$\rho_0 = 100/[(x/\rho x)+(y/\rho y)+(z/\rho z)+(100-x-y-z)/6.336] \quad (2)$$

x: blend ratio of zirconia containing 0.05 wt % of alumina and 3.0 mol % of yttria; wt % y: blend ratio of zirconia containing 0.05 wt % of alumina, 1,500 ppm of iron oxide and 3.0 mol % of yttria; wt % z: blend ratio of zirconia containing 0.05 wt % of alumina, 360 ppm of cobalt oxide and 3.0 mol % of yttria; wt %

The composition, the sintering temperature, and the measured density, relative density, total light transmittance by D65 light source, lightness value L*, value a* and value b* as chromatic parameters stipulated in JIS-Z8729, strength, crystal grain size and monoclinic phase transformation depth after immersion in hot water of 140° C. for 24 hours, of the obtained colored translucent zirconia sintered body, in Examples 21 to 32, are shown in the following Table 3.

TABLE 1

|  | Y$_2$O$_3$ (mol %) | Er$_2$O$_3$ (mol %) | Fe$_2$O$_3$ (ppm) | Al$_2$O$_3$ (wt %) | Sintering temperature (° C.) | Measured density (g/cm$^3$) | Relative density (%) | Total light transmittance (%) |
|---|---|---|---|---|---|---|---|---|
| Ex. 1 | 2.85 | 0.17 | 1430 | 0.05 | 1400 | 6.092 | 99.90 | 20.4 |
| Ex. 2 | 2.85 | 0.17 | 1430 | 0.05 | 1450 | 6.095 | 99.95 | 23.9 |
| Ex. 3 | 2.85 | 0.17 | 750 | 0.05 | 1400 | 6.091 | 99.89 | 29.6 |
| Ex. 4 | 2.85 | 0.17 | 750 | 0.05 | 1450 | 6.095 | 99.95 | 31.9 |
| Ex. 5 | 2.85 | 0.17 | 200 | 0.05 | 1400 | 6.092 | 99.89 | 36.7 |
| Ex. 6 | 2.85 | 0.17 | 200 | 0.05 | 1450 | 6.094 | 99.92 | 38.2 |
| Ex. 7 | 2.92 | 0.08 | 200 | 0.05 | 1450 | 6.095 | 99.95 | 39.0 |
| Ex. 8 | 2.92 | 0.08 | 450 | 0.05 | 1450 | 6.095 | 99.95 | 36.3 |
| Ex. 9 | 2.85 | 0.17 | 1430 | 0.05 | 1450 + HIP | 6.098 | 100 | 25.4 |
| Ex. 10 | 2.85 | 0.17 | 750 | 0.05 | 1450 + HIP | 6.098 | 100 | 33.1 |
| Ex. 11 | 2.85 | 0.17 | 200 | 0.05 | 1450 + HIP | 6.099 | 100 | 39.0 |
| Ex. 12 | 2.92 | 0.08 | 450 | 0.05 | 1450 + HIP | 6.098 | 100 | 38.4 |
| Comp. Ex. 1 | 3.00 | 0 | 200 | 0.05 | 1400 | 6.087 | 99.91 | 40.8 |
| Comp. Ex. 2 | 3.00 | 0 | 200 | 0.05 | 1450 | 6.087 | 99.91 | 40.8 |
| Comp. Ex. 3 | 3.00 | 0 | 450 | 0.05 | 1450 | 6.087 | 99.91 | 37.9 |

|  | L* | a* | b* | Strength (MPa) | Crystal grain size (μm) | Monoclinic phase transformation depth (μm) |
|---|---|---|---|---|---|---|
| Ex. 1 | 58.7 | 8.1 | 27.2 | — | 0.40 | 4 |
| Ex. 2 | 60.3 | 7.1 | 26.6 | 1041 | 0.43 | 9 |
| Ex. 3 | 65.8 | 4.5 | 20.4 | — | 0.41 | 2 |
| Ex. 4 | 66.3 | 3.6 | 19.0 | 1023 | 0.45 | 7 |
| Ex. 5 | 72.3 | 2.4 | 5.9 | — | 0.39 | 2 |
| Ex. 6 | 71.8 | 2.4 | 4.7 | — | 0.44 | 9 |
| Ex. 7 | 73.0 | 0.0 | 6.0 | — | 0.44 | — |
| Ex. 8 | 70.3 | 0.8 | 13.5 | — | — | — |
| Ex. 9 | 57.0 | 6.6 | 25.9 | — | — | — |
| Ex. 10 | 63.4 | 3.5 | 18.1 | — | — | — |
| Ex. 11 | 68.6 | 2.2 | 4.0 | — | — | — |
| Ex. 12 | 67.2 | 0.0 | 11.3 | — | — | — |
| Comp. Ex. 1 | 74.3 | −2.7 | 7.7 | — | 0.39 | 10 |
| Comp. Ex. 2 | 72.8 | −2.7 | 6.1 | 1180 | 0.41 | 13 |
| Comp. Ex. 3 | 71.2 | −2.2 | 10.7 | 1173 | 0.40 | 8 |

TABLE 2

|  | Y$_2$O$_3$ (mol %) | Er$_2$O$_3$ (mol %) | Fe$_2$O$_3$ (ppm) | Al$_2$O$_3$ (wt %) | Sintering temperature (° C.) | Measured density (g/cm$^3$) | Relative density (%) | Total light transmittance (%) |
|---|---|---|---|---|---|---|---|---|
| Ex. 13 | 2.40 | 0.66 | 1200 | 0.05 | 1450 | 6.133 | 99.92 | 24.9 |
| Ex. 14 | 2.70 | 0.33 | 1350 | 0.05 | 1450 | 6.113 | 99.93 | 24.1 |
| Ex. 15 | 2.70 | 0.33 | 1000 | 0.05 | 1450 | 6.113 | 99.95 | 27.8 |
| Ex. 16 | 2.70 | 0.33 | 200 | 0.05 | 1450 | 6.109 | 99.95 | 36.6 |
| Ex. 17 | 2.40 | 0.66 | 1200 | 0.05 | 1450 + HIP | 6.138 | 100 | 26.7 |
| Ex. 18 | 2.70 | 0.33 | 1350 | 0.05 | 1450 + HIP | 6.117 | 100 | 26.0 |
| Ex. 19 | 2.70 | 0.33 | 1000 | 0.05 | 1450 + HIP | 6.116 | 100 | 30.0 |
| Ex. 20 | 2.70 | 0.33 | 200 | 0.05 | 1450 + HIP | 6.112 | 100 | 38.6 |

|  | L* | a* | b* | Strength (MPa) | Crystal grain size (μm) | Monoclinic phase transformation depth (μm) |
|---|---|---|---|---|---|---|
| Ex. 13 | 60.2 | 8.3 | 22.5 | — | — | — |
| Ex. 14 | 60.6 | 7.6 | 25.6 | — | — | — |
| Ex. 15 | 63.8 | 6.3 | 22.0 | — | — | — |
| Ex. 16 | 70.5 | 5.2 | 3.6 | — | — | — |
| Ex. 17 | 57.0 | 7.3 | 20.2 | — | — | — |
| Ex. 18 | 57.1 | 6.4 | 23.4 | — | — | — |
| Ex. 19 | 60.1 | 5.0 | 19.5 | — | — | — |
| Ex. 20 | 67.0 | 3.8 | 1.6 | — | — | — |

TABLE 3

|  | Y$_2$O$_3$ (mol %) | Er$_2$O$_3$ (mol %) | Fe$_2$O$_3$ (ppm) | CoO (ppm) | Al$_2$O$_3$ (wt %) | Sintering temperature (° C.) | Measured density (g/cm$^3$) | Relative density (%) | Total light transmittance (%) |
|---|---|---|---|---|---|---|---|---|---|
| Ex. 21 | 2.87 | 0.40 | 400 | 0 | 0.05 | 1450 | 6.098 | 99.91 | 36.0 |
| Ex. 22 | 2.84 | 0.50 | 450 | 0 | 0.05 | 1450 | 6.100 | 99.90 | 36.2 |

TABLE 3-continued

| | | | | | | | | | |
|---|---|---|---|---|---|---|---|---|---|
| Ex. 23 | 2.84 | 0.50 | 650 | 0 | 0.05 | 1450 | 6.100 | 99.90 | 32.7 |
| Ex. 24 | 2.84 | 0.50 | 1000 | 0 | 0.05 | 1450 | 6.099 | 99.89 | 28.3 |
| Ex. 25 | 2.84 | 0.50 | 1300 | 0 | 0.05 | 1450 | 6.100 | 99.92 | 24.9 |
| Ex. 26 | 2.95 | 0.15 | 450 | 0 | 0.05 | 1450 | 6.089 | 99.86 | 36.4 |
| Ex. 27 | 2.94 | 0.20 | 600 | 0 | 0.05 | 1450 | 6.090 | 99.86 | 33.8 |
| Ex. 28 | 2.90 | 0.30 | 650 | 0 | 0.05 | 1450 | 6.094 | 99.89 | 33.4 |
| Ex. 29 | 2.87 | 0.40 | 1000 | 0 | 0.05 | 1450 | 6.095 | 99.87 | 27.3 |
| Ex. 30 | 2.84 | 0.50 | 1200 | 26 | 0.05 | 1450 | 6.098 | 99.88 | 22.6 |
| Ex. 31 | 2.97 | 0.10 | 450 | 0 | 0.05 | 1450 | 6.088 | 99.87 | 36.2 |
| Ex. 32 | 2.95 | 0.15 | 500 | 0 | 0.05 | 1450 | 6.090 | 99.87 | 35.8 |
| Ex. 33 | 2.94 | 0.20 | 650 | 5 | 0.05 | 1450 | 6.092 | 99.90 | 32.5 |
| Ex. 34 | 2.98 | 0.05 | 1000 | 0 | 0.05 | 1450 | 6.087 | 99.88 | 27.9 |
| Ex. 35 | 2.97 | 0.10 | 450 | 26 | 0.05 | 1450 | 6.090 | 99.90 | 31.0 |
| Ex. 36 | 2.95 | 0.15 | 700 | 26 | 0.05 | 1450 | 6.090 | 99.88 | 28.0 |
| Ex. 37 | 3.00 | 0 | 900 | 39 | 0.05 | 1450 | 6.086 | 99.88 | 23.6 |
| Ex. 38 | 2.97 | 0.10 | 1200 | 51 | 0.05 | 1450 | 6.088 | 99.88 | 19.4 |
| Ex. 39 | 2.94 | 0.20 | 900 | 26 | 0.05 | 1450 | 6.091 | 99.88 | 25.7 |
| Ex. 40 | 2.92 | 0.25 | 1000 | 8 | 0.05 | 1450 | 6.092 | 99.88 | 27.3 |
| Ex. 41 | 3.00 | 0 | 850 | 13 | 0.05 | 1450 | 6.086 | 99.88 | 28.6 |

| | L* | a* | b* | Strength (MPa) | Crystal grain size (μm) | Monoclinic phase transformation depth (μm) | Note |
|---|---|---|---|---|---|---|---|
| Ex. 21 | 70.9 | 1.8 | 11.0 | 1106 | — | — | A1(NCC) |
| Ex. 22 | 63.3 | 1.8 | 10.9 | — | — | — | A2(NCC) |
| Ex. 23 | 68.3 | 3.1 | 16.9 | 1100 | — | — | A3(NCC) |
| Ex. 24 | 64.0 | 4.8 | 22.8 | — | — | — | A3.5(NCC) |
| Ex. 25 | 61.9 | 6.3 | 25.4 | 1036 | — | — | A4(NCC) |
| Ex. 26 | 70.4 | −0.3 | 13.3 | — | — | — | A1(VITA) |
| Ex. 27 | 69.3 | 1.5 | 17.2 | — | — | — | A2(VITA) |
| Ex. 28 | 67.2 | 2.2 | 18.1 | — | — | — | A3(VITA) |
| Ex. 29 | 64.6 | 4.9 | 23.3 | — | — | — | A3.5(VITA) |
| Ex. 30 | 57.9 | 5.5 | 21.4 | — | — | 9 | A4(VITA) |
| Ex. 31 | 70.5 | −0.4 | 14.1 | — | — | — | B1(VITA) |
| Ex. 32 | 70.7 | 0.4 | 15.1 | — | — | — | B2(VITA) |
| Ex. 33 | 66.2 | 2.0 | 17.0 | 1055 | 0.41 | 10 | B3(VITA) |
| Ex. 34 | 65.8 | 3.5 | 23.9 | — | — | — | B4(VITA) |
| Ex. 35 | 64.4 | 1.5 | 10.5 | — | — | 10 | C1(VITA) |
| Ex. 36 | 62.2 | 2.5 | 15.6 | — | — | — | C2(VITA) |
| Ex. 37 | 59.3 | 2.9 | 17.7 | — | — | — | C3(VITA) |
| Ex. 38 | 55.8 | 4.6 | 20.1 | 1001 | 0.41 | 10 | C4(VITA) |
| Ex. 39 | 60.6 | 3.4 | 18.4 | — | — | — | D2(VITA) |
| Ex. 40 | 61.9 | 4.2 | 21.7 | — | — | — | D3(VITA) |
| Ex. 41 | 63.1 | 2.3 | 19.8 | — | — | 10 | D4(VITA) |

As is evident from these Tables, the colored translucent zirconia sintered bodies in Examples 1 to 20 have high relative densities at a level of at least 99.8% and also have high total light transmittances by D65 light source at a level of at least 18%, and thus, they are excellent colored translucent zirconia sintered bodies and expected to be utilized as dental materials such as a mill blank, an orthodontic bracket, etc.

Example 42

To a zirconium oxychloride aqueous solution, erbia was added to an $Er_2O_3$ concentration of 2.0 mol %, followed by hydrolysis to obtain a hydrated zirconia sol, which was then dried and calcined at a calcination temperature of 1,100° C. for 2 hours.

After washing the obtained calcined powder with water, α-alumina was mixed therewith to an alumina content of 0.05 wt %, and distilled water was added to obtain a slurry having a zirconia concentration of 45 wt %. This slurry was milled for 24 hours with a vibration mill using zirconia balls having a diameter of 3 mm.

The average particle size of the obtained slurry was 0.41 μm and the maximum particle size was ≤1.5 μm. The BET specific surface area of the dried zirconia powder was 13 $m^2$/g. To the obtained slurry, an organic binder was added in an amount of 3 wt %, and then a spray-drying was carried out to obtain a zirconia granulated powder having an average particle size of 50 μm.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to obtain a pink-colored zirconia sintered body.

Example 43

A milled slurry was obtained in the same manner as in Example 42 except that the $Er_2O_3$ concentration was changed to 3.0 mol %.

The average particle size of the obtained slurry was 0.43 μm and the maximum particle size was ≤1.5 μm. The BET specific surface area of the dried zirconia powder was 13 $m^2$/g. To the obtained slurry, an organic binder was added in an amount of 3 wt %, and then a spray-drying was carried out to obtain a zirconia granulated powder having an average particle size of 48 μm.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to obtain a pink-colored zirconia sintered body.

Example 44

A milled slurry was obtained in the same manner as in Example 42 except that the $Er_2O_3$ concentration was changed to 3.2 mol %.

The average particle size of the obtained slurry was 0.42 µm and the maximum particle size was ≤1.5 µm. The BET specific surface area of the dried zirconia powder was 12 m²/g. To the obtained slurry, an organic binder was added in an amount of 3 wt %, and then a spray-drying was carried out to obtain a zirconia granulated powder having an average particle size of 49 µm.

The obtained granulated powder was molded by uniaxial pressing (19.6 MPa), then molded by CIP (196 MPa) and sintered (pressureless sintering) under conditions of a sintering temperature of 1,400° C., a temperature-rising rate of 600° C./hr, and a retention time of 2 hours, to obtain a pink-colored zirconia sintered body.

Example 45

A pink-colored zirconia sintered body was produced in the same manner as in Example 44 except that the sintering temperature was changed to 1,450° C.

Comparative Example 4

A milled slurry was obtained in the same manner as in Example 42 except that the $Er_2O_3$ concentration was changed to 4.0 mol %.

The average particle size of the obtained slurry was 0.42 µm and the maximum particle size was ≤1.5 µm. The BET specific surface area of the dried zirconia powder was 12 m²/g. To the obtained slurry, an organic binder was added in an amount of 3 wt %, and then a spray-drying was carried out to obtain a zirconia granulated powder having an average particle size of 50 µm.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to obtain a pink-colored zirconia sintered body.

The obtained zirconia sintered body was a sintered body having low strength.

Comparative Example 5

A milled slurry was obtained in the same manner as in Example 42 except that the $Er_2O_3$ concentration was changed to 5.0 mol %.

The average particle size of the obtained slurry was 0.42 µm and the maximum particle size was ≤1.5 µm. The BET specific surface area of the dried zirconia powder was 12 m²/g. To the obtained slurry, an organic binder was added in an amount of 3 wt %, and then a spray-drying was carried out to obtain a zirconia granulated powder having an average particle size of 47 µm.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to obtain a pink-colored zirconia sintered body.

The obtained zirconia sintered body was a sintered body having low strength.

Comparative Example 6

A milled slurry was obtained in the same manner as in Example 42 except that the $Er_2O_3$ concentration was changed to 1.5 mol %.

The average particle size of the obtained slurry was 0.41 µm and the maximum particle size was ≤1.5 µm. The BET specific surface area of the dried zirconia powder was 13 m²/g. To the obtained slurry, an organic binder was added in an amount of 3 wt %, and then a spray-drying was carried out to obtain a zirconia granulated powder having an average particle size of 47 µm.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to sinter a pink-colored zirconia.

However, the green body was disintegrated without maintaining its shape and could not be sintered.

Example 46

A milled slurry was obtained in the same manner as in Example 42 except that yttria and erbia were added to the zirconium oxychloride aqueous solution to bring the $Y_2O_3$ concentration to be 1.7 mol % and the $Er_2O_3$ concentration to be 1.4 mol %.

The average particle size of the obtained slurry was 0.43 µm and the maximum particle size was ≤1.5 µm. The BET specific surface area of the dried zirconia powder was 13 m²/g. To the obtained slurry, an organic binder was added in an amount of 3 wt %, and then a spray-drying was carried out to obtain a zirconia granulated powder having an average particle size of 50 µm.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to obtain a pink-colored zirconia sintered body.

Example 47

A milled slurry was obtained in the same manner as in Example 42 except that yttria and erbia were added to the zirconium oxychloride aqueous solution to bring the $Y_2O_3$ concentration to be 2.8 mol % and the $Er_2O_3$ concentration to be 0.3 mol %.

The average particle size of the obtained slurry was 0.42 µm and the maximum particle size was ≤1.5 µm. The BET specific surface area of the dried zirconia powder was 14 m²/g. To the obtained slurry, an organic binder was added in an amount of 3 wt %, and then a spray-drying was carried out to obtain a zirconia granulated powder having an average particle size of 48 µm.

The obtained granulated powder was molded by uniaxial pressing (19.6 MPa), then molded by CIP (196 MPa) and sintered (pressureless sintering) under conditions of a sintering temperature of 1,450° C., a temperature-rising rate of 600° C./hr, and a retention time of 2 hours, to obtain a pink-colored zirconia sintered body.

Example 48

A pink-colored zirconia sintered body was produced in the same manner as in Example 44 except that α-alumina was added to an alumina content of 0.10 wt %.

Example 49

A pink-colored zirconia sintered body was produced in the same manner as in Example 48 except that the sintering temperature was changed to 1,450° C.

Example 50

A pink-colored zirconia sintered body was produced in the same manner as in Example 44 except that α-alumina was added to an alumina content of 0.15 wt %.

Example 51

A pink-colored zirconia sintered body was produced in the same manner as in Example 50 except that the sintering temperature was changed to 1,450° C.

Comparative Example 7

A pink-colored zirconia sintered body was produced in the same manner as in Example 45 except that no α-alumina was added.

The obtained zirconia sintered body was a sintered body poor in hydrothermal deterioration resistance.

Comparative Example 8

A pink-colored zirconia sintered body was produced in the same manner as in Example 44 except that α-alumina was added to an alumina content of 0.25 wt %.

The obtained zirconia sintered body was a sintered body having a low density.

Comparative Example 9

A pink-colored zirconia sintered body was produced in the same manner as in Comparative Example 8 except that the sintering temperature was changed to 1,450° C.

The obtained zirconia sintered body was a sintered body having a low density.

The erbia amount, the yttria amount, the alumina additive amount, the sintering temperature, and the measured density, relative density, total light transmittance by D65 light source, lightness value L*, value a* and value b* as chromatic parameters stipulated in JIS-Z8729, three-point bending strength, average crystal grain size and monoclinic phase transformation depth after immersion in hot water of 140° C. for 24 hours, of the obtained colored translucent zirconia sintered body, in Examples 42 to 51 and Comparative Examples 4 to 9, are shown in the following Table 4.

TABLE 4

|  | $Er_2O_3$ (mol %) | $Y_2O_3$ (mol %) | $Al_2O_3$ (wt %) | Sintering temperature (° C.) | Measured density (g/cm³) | Relative density (%) | Total light transmittance (%) |
| --- | --- | --- | --- | --- | --- | --- | --- |
| Ex. 42 | 2.0 | 0 | 0.05 | 1450 | 6.261 | 99.94 | 30.0 |
| Ex. 43 | 3.0 | 0 | 0.05 | 1450 | 6.321 | 99.93 | 29.3 |
| Ex. 44 | 3.2 | 0 | 0.05 | 1400 | 6.330 | 99.91 | 27.9 |
| Ex. 45 | 3.2 | 0 | 0.05 | 1450 | 6.332 | 99.94 | 28.9 |
| Ex. 46 | 1.4 | 1.7 | 0.05 | 1450 | 6.189 | 99.93 | 33.2 |
| Ex. 47 | 0.3 | 2.8 | 0.05 | 1450 | 6.104 | 99.90 | 38.8 |
| Comp. Ex. 4 | 4.0 | 0 | 0.05 | 1450 | 6.384 | 99.92 | 29.8 |
| Comp. Ex. 5 | 5.0 | 0 | 0.05 | 1450 | 6.389 | 99.93 | 32.2 |
| Comp. Ex. 6 | 1.5 | 0 | 0.05 | 1450 | — | — | — |
| Ex. 48 | 3.2 | 0 | 0.10 | 1400 | 6.329 | 99.89 | 28.2 |
| Ex. 49 | 3.2 | 0 | 0.10 | 1450 | 6.330 | 99.91 | 28.9 |
| Ex. 50 | 3.2 | 0 | 0.15 | 1400 | 6.327 | 99.86 | 27.8 |
| Ex. 51 | 3.2 | 0 | 0.15 | 1450 | 6.328 | 99.87 | 28.4 |
| Comp. Ex. 7 | 3.2 | 0 | 0 | 1450 | 6.335 | 99.95 | 29.1 |
| Comp. Ex. 8 | 3.2 | 0 | 0.25 | 1400 | 6.316 | 99.75 | 26.8 |
| Comp. Ex. 9 | 3.2 | 0 | 0.25 | 1450 | 6.317 | 99.76 | 27.0 |

|  | L* | a* | b* | Three-point bending strength (MPa) | Average crystal grain size (μm) | Monoclinic phase transformation depth (μm) |
| --- | --- | --- | --- | --- | --- | --- |
| Ex. 42 | 63.6 | 16.7 | −4.6 | 1178 | 0.40 | 4 |
| Ex. 43 | 62.2 | 19.3 | −6.5 | 1056 | 0.41 | 13 |
| Ex. 44 | 60.9 | 18.6 | −5.3 | — | 0.39 | 4 |
| Ex. 45 | 59.6 | 18.5 | −5.2 | 1082 | 0.43 | 10 |
| Ex. 46 | 68.0 | 14.1 | −5.6 | 1102 | 0.41 | 13 |
| Ex. 47 | 70.6 | 4.9 | −4.3 | 1119 | 0.43 | 9 |
| Comp. Ex. 4 | 56.8 | 20.2 | −8.4 | 864 | 0.48 | 0 |
| Comp. Ex. 5 | 55.9 | 21.8 | −9.3 | 645 | 0.55 | 0 |
| Comp. Ex. 6 | — | — | — | — | — | — |
| Ex. 48 | 61.1 | 18.9 | −6.8 | — | 0.40 | — |
| Ex. 49 | 61.0 | 19.1 | −6.5 | 1090 | 0.42 | 7 |
| Ex. 50 | 61.4 | 19.2 | −6.7 | — | 0.39 | — |
| Ex. 51 | 60.9 | 19.1 | −5.9 | 1075 | 0.42 | 4 |
| Comp. Ex. 7 | 60.8 | 19.0 | −6.3 | 1066 | 0.41 | 21 |
| Comp. Ex. 8 | 64.5 | 19.3 | −5.7 | — | 0.40 | — |
| Comp. Ex. 9 | 64.2 | 19.3 | −5.5 | 1059 | 0.42 | 5 |

As is evident from this Table, the pink-colored zirconia sintered bodies in Examples 42 to 51 are pink-colored zirconia sintered bodies which have large values L* and thus high lightness, large values a* and thus bright pink color, and high relative densities at a level of at least 99.8% and also have high strength at a level of at least 1,000 MPa, and thus, they are expected to be utilized as decorative members or exterior packages for electronic devices.

INDUSTRIAL APPLICABILITY

The colored translucent zirconia sintered body of the present invention has high sintered body density and strength, has a color tone quite similar to the color tone of natural teeth and further is excellent in translucency, and therefore, it is particularly suitable for a zirconia sintered body to be used for dental applications, and further, suitable for a mill blank such as an artificial tooth material or the like, and an orthodontic bracket.

The pink-colored zirconia sintered body of the present invention is a sintered body having high strength and excellent aesthetic properties and thus is useful as a decorative member or an exterior package for electronic material.

The entire disclosures of Japanese Patent Application No. 2012-286955 filed on Dec. 28, 2012, Japanese Patent Application No. 2012-286957 filed on Dec. 28, 2012 and Japanese Patent Application No. 2013-174623 filed on Aug. 26, 2013 including specifications, claims and summaries are incorporated herein by reference in their entireties.

The invention claimed is:

1. A colored translucent zirconia sintered body which comprises from 2 to 4 mol % of yttria, from 0.02 to 0.8 mol % of $Er_2O_3$, at least 20 and less than 2,000 ppm, as calculated as $Fe_2O_3$, of an iron compound, at least 0.005 and less than 0.2 wt % of $Al_2O_3$ and the rest being zirconia, and which has a lightness L* of from 55 to 75, a* of from 0 to 10 and b* of from 0 to 30 as chromatic parameters stipulated in JIS-Z8729, has a relative density of at least 99.80% and has a total light transmittance of at least 18% and at most 40% as measured at a sample thickness of 1 mm using a D65 light source.

2. A colored translucent zirconia sintered body which comprises from 2 to 4 mol % of yttria, less than 0.01 wt %, as calculated as CoO, of cobalt oxide, at least 20 and less than 2,000 ppm, as calculated as $Fe_2O_3$, of an iron oxide, at least 0.005 and less than 0.2 wt % of $Al_2O_3$ and the rest being zirconia, and which has a lightness L* of from 50 to 75, a* of from −1 to 10 and b* of from 0 to 30 as chromatic parameters stipulated in JIS-Z8729, has a relative density of at least 99.80% and has a total light transmittance of at least 18% and at most 40% as measured at a sample thickness of 1 mm using a D65 light source.

3. The colored translucent zirconia sintered body according to claim 2, which contains from 0.02 to 0.8 mol % of $Er_2O_3$ as a part of said rest.

4. The colored translucent zirconia sintered body according to claim 2, wherein the lightness L*, a* and b* as chromatic parameters stipulated in JIS-Z8729, are within the following ranges:

L* is from 50 to 75,
a* is from −1 to 7,
b* is from 10 to 27, $$a^* > 0.0123 b^{*2} - 0.0598 b^* - 2.9088$$

5. The colored translucent zirconia sintered body according to claim 1, which has a crystal grain size of from 0.35 to 0.50 μm.

6. The colored translucent zirconia sintered body according to claim 1, which has a monoclinic phase transformation depth of from 0 to 15 μm after immersion in hot water of 140° C. for 24 hours.

7. The colored translucent zirconia sintered body according to claim 1, which has a three-point bending strength of at least 1,000 MPa.

8. A dental material obtained by using the colored translucent zirconia sintered body as defined in claim 1.

9. A pink-colored zirconia sintered body which is stabilized solely by erbia ($Er_2O_3$) or stabilized by yttria ($Y_2O_3$) and erbia ($Er_2O_3$), further contains at least 0.005 wt % and less than 0.2 wt % of alumina, and contains, when stabilized solely by erbia, at least 2 mol % and less than 4 mol % of erbia, or, when stabilized by erbia and yttria, at least 0.1 mol % and less than 2 mol % of erbia and at least 1 mol % and less than 4 mol % of yttria, and which has a lightness L* of from 58 to 75, a* of from 3 to 20 and b* of from −8 to −4 as chromatic parameters stipulated in JIS-Z8729.

10. The pink-colored zirconia sintered body according to claim 9, which has a total light transmittance of at least 25% as measured at a sample thickness of 1 mm using a D65 light source.

11. The pink-colored zirconia sintered body according to claim 9, which has a relative density of at least 99.80%.

12. The pink-colored zirconia sintered body according to claim 9, which has a crystal grain size of from 0.35 to 0.50 μm.

13. The pink-colored zirconia sintered body according to claim 9, which has a monoclinic phase transformation depth of from 0 to 15 μm after immersion in hot water of 140° C. for 24 hours.

14. The pink-colored zirconia sintered body according to claim 9, which has a three-point bending strength of at least 1,000 MPa.

15. The colored translucent zirconia sintered body according to claim 2, which has a crystal grain size of from 0.35 to 0.50 μm.

16. The colored translucent zirconia sintered body according to claim 2, which has a monoclinic phase transformation depth of from 0 to 15 μm after immersion in hot water of 140° C. for 24 hours.

17. The colored translucent zirconia sintered body according to claim 2, which has a three-point bending strength of at least 1,000 MPa.

18. A dental material obtained by using the colored translucent zirconia body as defined in claim 2.

* * * * *